(12) United States Patent
Cook et al.

(10) Patent No.: US 9,861,384 B1
(45) Date of Patent: Jan. 9, 2018

(54) TROCAR AND SHEATH ASSEMBLY FOR PLACEMENT OF IMPLANTABLE DEVICE ADJACENT A BODY LUMEN

(71) Applicant: Uromedica, Inc., Plymouth, MN (US)

(72) Inventors: Timothy C. Cook, Wayzata, MN (US); John H. Burton, Minnetonka, MN (US); James E. Cabak, Plymouth, MN (US)

(73) Assignee: Uromedica, Inc., Plymouth, MN (US)

(*) Notice: Subject to any disclaimer, the term of this patent is extended or adjusted under 35 U.S.C. 154(b) by 43 days.

(21) Appl. No.: 14/517,143

(22) Filed: Oct. 17, 2014

Related U.S. Application Data

(60) Provisional application No. 61/892,960, filed on Oct. 18, 2013.

(51) Int. Cl.
| | | |
|---|---|---|
| *A61B 17/34* | (2006.01) | |
| *A61B 17/3203* | (2006.01) | |
| *A61F 2/00* | (2006.01) | |
| *A61M 19/00* | (2006.01) | |

(52) U.S. Cl.
CPC ...... *A61B 17/3403* (2013.01); *A61B 17/3203* (2013.01); *A61B 17/3468* (2013.01); *A61F 2/004* (2013.01); *A61M 19/00* (2013.01); *A61B 2017/3413* (2013.01)

(58) Field of Classification Search
CPC ............ A61B 17/3403; A61B 17/3203; A61B 17/3468; A61F 2/004; A61M 19/00
See application file for complete search history.

(56) References Cited

U.S. PATENT DOCUMENTS

| | | | | |
|---|---|---|---|---|
| 8,926,494 | B1* | 1/2015 | Cook | A61B 8/085 600/30 |
| 2002/0143234 | A1* | 10/2002 | LoVuolo | A61B 17/06109 600/30 |
| 2012/0330340 | A1* | 12/2012 | Shohat | A61B 8/12 606/190 |
| 2015/0173708 | A1* | 6/2015 | Cook | A61B 8/085 600/439 |

* cited by examiner

*Primary Examiner* — Michael Rozanski
(74) *Attorney, Agent, or Firm* — Schwegman Lundberg & Woessner, P.A.

(57) ABSTRACT

The present subject matter provides a trocar and sheath assembly for placement of implantable devices adjacent a body lumen, and a method of using the trocar and sheath assembly for implanting an implantable device at a target site for controllable coaptation of a patient's urethra.

21 Claims, 16 Drawing Sheets

SLOTTED TROCAR WITH OVER THE WIRE DELIVERY

TROCAR AND SHEATH ASSEMBLY FOR PLACEMENT OF IMPLANTABLE DEVICE ADJACENT A BODY LUMEN

CROSS REFERENCE TO RELATED APPLICATIONS

The present application claims the benefit of the filing date of U.S. application Ser. No. 61/892,960, filed on Oct. 18, 2013, the disclosure of which is incorporated by reference herein.

FIELD OF THE INVENTION

The present subject matter relates to methods and apparatus to assist in introducing implantable devices for treating urinary incontinence.

BACKGROUND

Incontinence is a complex disorder with often more than one cause, a factor that has complicated the search for effective solutions. The five major categories of incontinence include: overflow, urge, stress, mixed (combination of both urge and stress), and functional. Male incontinence makes up approximately 15% (1.4 million) of the urinary incontinence population (male and female) with the majority experiencing mixed incontinence, followed by urge or stress incontinence. Stress urinary incontinence is a well-known complication of radical prostatectomy and transurethral resection of the prostate (TURP).

Several large studies have examined the median probability for developing stress urinary incontinence following all forms of surgery for benign prostatic hyperplasia (BPH). The European Association of Urology (EAU) and the American Urological Association (AUA), as well as the National Health and Medical Research Council (NHMRC) of Australia have all conducted extensive literature searches and reviews, examining the outcomes of surgeries for BPH. Incontinence rates reported by these three reviews following transurethral incision of the prostate (TUIP) range between 0.1%-0.75%, and following TURP between 1%-2.2%. Open prostatectomy produces between 0.5%-1.9% incontinent patients. The NHMRC summary reported total incontinence and stress incontinence separately, with the incidence of 1% (90% CI 0.7-14%) and 2.1% (90% CI 1.75-2.5%) respectively found in the literature. Of the three operations, TURP is the most widely and commonly employed procedure. Approximately 195,000 TURPs are performed annually in the USA.

Benoit et al. (*Urol.*, 56:116 (2000)) examined the records of 25,651 men who were reported under Medicare statistics in 1991 as having undergone a radical retropubic prostatectomy (RRP) for cancer of the prostate. Nearly 22% (5573 of 25,651 men) reported incontinence post RRP and at 12 months post-RRP, 8% (2025 men) continued to carry this diagnosis.

The largest study to date to assess the frequency of diagnosis of prostate carcinoma and post prostatectomy incontinence is Mittlin et al. (*Cancer*, 83:1679 (1995)). Data from 1,114 hospitals and 103,979 subjects diagnosed with prostate cancer in 1992 were surveyed. The survey team defined regular urinary incontinence as an unwanted loss of urine at least twice over the past month. The results demonstrated the overall rate of incontinence to be up to 20-22% in the community dwelling patients and that the surgical mortality rates from the surgery were approximately one percent.

The majority of men with incontinence associated with various forms of prostatectomy are conservatively managed using absorbent products (pads/adult diapers) or occlusive products (penile clamps) while the patient "watches and waits" to see whether improvement will occur with the passage of time. Most reports on post-prostatectomy incontinence and its treatment agree that a follow-up period of at least 12 months is necessary before confirming an individual's status as one of established incontinence.

Stress urinary incontinence has a high probability of natural resolution within the first year post-surgery (Mebust, Chapter 49 in *Campbell's Urology*, p. 1511 (1998)). During this period several therapies, such as pelvic floor training, medication, and bulking agents, may be helpful in restoring continence sooner, but differences compared with no treatment typically disappear by 12 months post-procedure. Stress incontinence lasting longer than 12 months, and/or not responding to conservative treatment may be improved using surgically implanted devices. Devices include the Artificial Urethral Sphincter (AUS) and sub-urethral slings.

The AUS is currently considered the gold standard for treatment for chronic stress urinary incontinence especially severe cases. The implantation of device qualifies as a major procedure with required surgical placement of several components including the circumferential urethral cuff, the pressure-regulating balloon, and the scrotal pump which controls inflation and deflation of the urethral cuff for continence. This cuff mechanism eliminates passage of urine; the recipient manipulates the device to open the urethra. Manipulation requires some manual dexterity. Revisions of the AUS typically involve surgical risks consistent with the original procedure. With AUS, the reoperation rate is found to be 22-25% but the reoperation rate is both complicated and invasive.

Sub-urethral slings represent a variety of devices based on passive, semi-circumferential urethral compression. Devices differ in material and in how and/or where they are anchored. Most are fixed, like the AUS, but a few feature adjustable tension, e.g. Remeex System (K062341). Published literature reviews (Mebust, supra, and Borgermann et al., 107:454 (2010)) suggest improvement rates (less stringent than social continence) of 75% to 90% with easier implantation and fewer adverse events and revisions than the AUS in mild to moderate cases. The most common adverse events reported were infection, 0% to 6%, urethral erosion, 0% to 2% and post implant scrotum pain or numbness resolving within three months, 16% to 72%. Urethral slings are cheaper and less invasive and show dry rates of 42-70% (Rocha et al., *Urol.*, 71:85 (2005)). Slings however, carry a considerable risk of urinary retention and pain (Herschorn et al., *Neurol. Urodyn.*, 29:179 (2010)). Less invasive treatments, such as the injection of a bulking agent (Macrroplastique) in the external sphincter, have also been tried but the long-term results are poor: only 25% of the patients have any treatment effect on pad use after 12 months (Stein et al., *J. Urol.*, 173:1654 (2005)).

SUMMARY

The present subject matter provides methods and apparatus to assist in the placement of implantable devices adjacent a body lumen. For example, an incision is made and a needle is inserted through solid tissue until the needle tip is near the target site, then the needle is withdrawn. In one embodiment, an incision is made near the perineum, for instance, two small incisions of approximately 1.0 cm one on each side of the perineal midline, and a needle is inserted through tissue until the needle tip is near the target site, e.g., anastomosis, then, in one embodiment, the needle is withdrawn. In one embodiment, a guidewire, e.g., a flexible guidewire such as one with a coil around a single straight wire or a wire with a J-tip, or a stylet, e.g., a stiff solid wire, is inserted through or adjacent to the needle. In one embodiment, a trocar, e.g., a mated trocar, enveloped in a U-channel sheath (a trocar/sheath assembly) is then inserted, with ultrasound guidance if necessary. In one embodiment, the assembly is inserted into tissue over the guidewire or stylet, e.g., the trocar has a lumen which is employed to advance the assembly over the guidewire or stylet, and then the trocar, and optionally the guidewire or stylet, is/are withdrawn. A sheath can be used to introduce other devices, e.g., implantable devices, to the target site. Fluoroscopy may be used to confirm the position of one or more of the needle, trocar, sheath or implantable device. Some methods include the use of ultrasound for placement of the needle, trocar/sheath assembly and/or implantable devices. Some apparatus are provided to improve imaging of the desired target site for positioning of the implantable devices. Such apparatus may be used to deliver echogenic material including anesthetic, analgesic or other types of material, or combinations thereof, either serially or concomittently. Such apparatus may be used for hydrodissection. In one embodiment, a needle delivers an anesthetic or analgesic and is employed for hydrodissection.

The implantation instruments for use in the methods include, but are not limited to, a sharp tip trocar and a U-channel (or U-shaped) sheath and optionally a blunt trocar and/or tissue expanding device (TED). The sharp trocar/U-channel sheath creates a path for the implantable device and the hydrodissection prepares the tissue cavity for device insertion. A blunt trocar may replace the pointed trocar within the U-channel sheath for dilation near the bladder neck. In one embodiment, a blunt tip trocar and a U-channel (or U-shaped) sheath and/or tissue expanding device (TED) is employed. Once the tip of the trocar is correctly located along the distal urethra near the bladder neck, the instrument is uncoupled from the U-channel sheath and removed, leaving the sheath in place. The TED may then be used to dilate tissue at the site where the balloon is implanted by inserting and locking the TED in the U-channel sheath, then squeezing the TED handles to open the jaw, facilitating tissue dilation. The TED is then removed from the U-channel sheath.

In one embodiment, the implantable device delivered through the sheath consists of a balloon, tube or bi-lumen tube and subcutaneous port. The device may be formed from medical grade silicone elastomer. The injection port may be made from titanium covered in silicone elastomer. In one embodiment, the device is about 10 cm to about 15 cm, e.g., 12 cm or 14 cm, in overall length. The length of the tubing between the balloon and the titanium injection port allows for the difference in length. The tubing that connects the balloon and the injection port has one lumen used for inflation of the balloon and another for delivery of the implantable device into the tissue using a previously placed push wire. The push wire may be made of medical grade stainless steel and provides sufficient column strength to allow the device to be inserted to the correct position. Once the correct placement of the device has been confirmed, the push wire is removed. In one embodiment, the balloon is spherical for the greatest tissue displacement effect in a medio-lateral direction with a volume variation of 0.5 milliliters up to 8.0 milliliters per balloon. Two balloons are placed on either side of the urethra at the bladder neck. Each balloon may be filled with an isotonic mixture of sterile water and radiopaque contrast so that the balloon can be imaged at the bladder neck. The ports of the two devices may be placed in the posterior side of the scrotum so that percutaneous access by a needle of the ports for volume adjustment is easily attained at a later time.

Thus, the invention provides a surgical instrument for penetrating tissue. For example, the instrument includes a trocar with a lumen, the trocar having a distal end including a penetrating tip disposed at one end thereof, and optionally a handle. The trocar may be formed by mating of two independent trocar portions, e.g., each along a central longitudinal axis, wherein the inner face of each portion is concave and the mating forms a channel (lumen), e.g., of less than about 5 mm, 4 mm, 3 mm, 2 mm or smaller in diameter, such as less than 1 mm in diameter. In one embodiment the lumen is about 0.5 mm to about 2 mm in diameter. A trocar assembly may include an elongated U-shaped sheath dimensioned and structured to removably receive the trocar. The sheath includes an elongated shaft in a U-shape, forming an interior, centrally disposed passage or lumen. The elongated shaft allows for the penetrating tip at the distal end of the trocar shaft to extend outward in the assembly. The penetrating instrument is designed and structured to effectively create a small access opening by penetrating through underlying body tissue of a patient in a manner which serves to separate and enlarge the opening created by a needle, as the penetrating tip and shaft of the trocar/sheath assembly pass there-through. The overall structure, configuration, dimension and disposition of the penetrating instrument is such as to accomplish an effective separation of the bodily tissue being penetrated with a minimal application of an inwardly directed linear force. In doing so, the structure of the penetrating instrument dilates the outer tissue in a manner which minimizes damage to the tissue. The penetrating tip of the trocar is cooperatively disposed, dimensioned and configured relative to and/or with the sheath. The penetrating tip includes a base and a distal extremity configured to define an apex. The term apex includes a variety of different configurations, which may vary from a sharpened point to a tapered locale, as may be defined by the converging of the penetrating tip's exterior surface from a base thereof and extending continuously to the distal extremity or apex. In one embodiment of the present invention, the apex of the penetrating tip is spaced laterally outward or in an off-set position relative to the central longitudinal access of the sheath shaft.

In one embodiment, the invention provides a method of preparing a conduit in body tissue for implanting an implantable device to improve coaptation of the urethra at a target site for controllable coaptation of a patient's urethra, e.g., a male patient. The method includes placing a small puncture in the perineum of the patient, passing a needle through the puncture, while optionally delivering anesthetic during passage, to the target site under ultrasonic guidance, e.g., biplanar ultrasound, placing a guidewire or stylet through or adjacent to the needle and withdrawing the needle. In one embodiment, a trocar, e.g., a mated trocar, and U-shaped sheath assembly is delivered over the guidewire or stylet to the target site. In one embodiment, the trocar is formed of at least two longitudinally mated portions that, once assembled, form an inner lumen, and wherein the U-shaped sheath has an interior space and is configured to fit over the outer circumference of the trocar. The trocar, and optionally the guidewire or stylet, is removed and optionally the sheath is advanced. The implantable device is delivered via the interior space of the U-shaped sheath. In one embodiment, the method further comprises injecting echogenic fluid, e.g., water or an analgesic, at the target site adjacent the urethra. In one embodiment, injecting includes hydrodissecting the target site with the fluid to create a pocket for the implantable device. In one embodiment, placing a small puncture includes placing a small puncture in the perineum using a spinal needle, hubless needle or a needle with a removable hub, and passing the needle through to the target site. In one embodiment, the assembly is delivered to the target site under ultrasonic guidance. In one embodiment, the trocar and/or sheath is/are formed of stainless steel. In one embodiment, the trocar and/or sheath is/are formed of a synthetic polymer, e.g., polyethylene or polypropylene. In one embodiment, the inner lumen of the assembled mated trocar has a diameter of less than about 0.5 mm. In one embodiment, the inner lumen of the assembled trocar has a diameter of less than about 1.0 mm.

In one embodiment, the invention provides a method of preparing a conduit in body tissue for implanting an implantable device to improve coaptation of the urethra at a target site for controllable coaptation of a patient's urethra, i.e., a male or female patient. The method includes placing a small puncture in the perineum of the patient, passing a needle through the puncture, while optionally delivering anesthetic during passage, to the target site under ultrasonic guidance, placing a guidewire or stylet through or adjacent to the needle and withdrawing the needle. In one embodiment, a trocar, e.g., a tip capture trocar, and U-shaped sheath assembly is delivered over the guidewire or stylet to the target site, and wherein the U-shaped sheath has an interior space and is configured to fit over the outer circumference of the trocar. The tip capture trocar has a beveled receptacle at its distal tip such that it can attach to or house a proximal portion of a guidewire, stylet or needle and is slid down to the distal tip of the guidewire, stylet or needle, and which is retained in a slot along the side of the trocar. The trocar and the guidewire, stylet or needle are removed, and optionally the sheath is advanced, before delivering the implantable device via the interior space of the U-shaped sheath. In one embodiment, the method further comprises injecting echogenic fluid, e.g., water or an analgesic, at the target site adjacent the urethra. In one embodiment, injecting includes hydrodissecting the target site with the fluid to create a pocket for the implantable device. In one embodiment, placing a small puncture includes placing a small puncture in the perineum using a spinal needle, hubbed needle, hubless needle or removable hub needle, and passing the needle through to the target site. In one embodiment, the assembly is delivered to the target site under ultrasonic guidance. In one embodiment, the trocar and/or sheath is/are formed of stainless steel. In one embodiment, the trocar and/or sheath is/are formed of a synthetic polymer. In one embodiment, the inner lumen of the assembled trocar has a diameter of less than about 0.5 mm. In one embodiment, the inner lumen of the assembled trocar has a diameter of less than about 1.0 mm.

The invention also provides a method of mating a trocar. The method includes providing a first portion of a trocar and a second portion of a trocar, wherein the first portion has a recess at the distal end and the second portion has a protruding distal end, and wherein the inner longitudinal face of each portion is concave; inserting the protruding distal end of the second portion into the recess of the first portion so that the concave portions from each trocar portion form a lumen of less than about 1 mm in diameter, thereby forming an assembled trocar. In one embodiment, the method includes inserting the assembled trocar into a sheath. In one embodiment, the sheath is a U-shaped sheath. In one embodiment, the method includes passing a liquid, gas, wire, tube, and/or other instrument through the lumen.

Also provided is a system for implanting an adjustable continence device into a patient having a bladder with a bladder neck, the adjustable continence device comprising an adjustable balloon and a self sealing port. The system includes a trocar including a length and a width, the trocar or one of the mated portions thereof is coupled to a handle and sized to extend from an incision in the patient to the bladder neck of the patient. In one embodiment, the trocar is formed of at least two mated portions that once assembled form an inner lumen, wherein one portion has a recess at the distal end and the second portion has a tab extending at the distal end that is configured to fit into the recess. In one embodiment, the trocar is a tip capture trocar having a beveled receptacle at its distal tip such that it can attach to a proximal portion of a guidewire, stylet or needle and a slot along its side; and a U-shaped sheath defining an interior space sized to removably and slidably receive the trocar, the sheath including a slot running at least partially along a first portion, and tube shaped along a second portion and defining a lumen along the second portion. In one embodiment, the interior space is sized to slidably receive the adjustable continence device and a lumen of the device is sized to slidably receive a pushwire to push the adjustable continence device through the interior space. In one embodiment, the trocar includes a sharp tip at a distal end of the trocar, with the handle being at a proximal end of the trocar. In one embodiment, the handle is on one of the two mated parts. In one embodiment, the trocar includes a blunt tip at a distal end of the trocar, with the handle being at a proximal end of the trocar. In one embodiment, the trocar and/or the sheath includes stainless steel.

Further provided is a method for implanting a first adjustable continence device comprising an adjustable balloon and a self sealing port. The method includes inserting a trocar into a U-shaped sheath to form an assembly. In one embodiment, the trocar is formed of at least two mated portions that once assembled form an inner lumen, wherein one portion has a recess at the distal end and the second portion has a tab that is configured to fit into the recess. In one embodiment, the trocar is a tip capture trocar having at a distal end a receptacle for a tip of a needle, guidewire or stylet and an off center opening. The U-shaped sheath is sized to removably and slidably receive the trocar, the sheath including a slot running at least partially along a first portion and defining an interior space, and tube shaped along a second portion and defining a lumen, wherein the interior space and lumen are sized to slidably receive the adjustable continence device. The assembly is inserted into a first incision and through tissue until a tip of the trocar is proximal an exterior of a bladder of the patient and proximal a bladder neck of the bladder; removing the trocar from the sheath; inserting a first implantable adjustable continence device through the sheath and into the patient proximal the exterior of the bladder and proximal the bladder neck of the bladder; adjusting the first implantable adjustable device using a syringe coupled to the self sealing port; and removing the sheath from the patient. In one embodiment, the adjustable device is inserted into the interior space of the sheath such that the self sealing port is not in the interior space. In one embodiment, the method includes pushing the implantable adjustable device into the patient using a pushwire that extends into the lumen of the implantable device, e.g., removing the sheath while the implantable device is inserted into the patient.

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their legal equivalents.

BRIEF DESCRIPTION OF THE DRAWINGS

FIG. 14 shows the mating of portions of a slotted trocar and FIG. 14 shows a sheath. The portion of the trocar at the top of FIG. 14 (and the bottom of FIG. 15) has a tab at the distal end and aligns with the other portion, e.g., between the handles. An enlarged view of the distal ends of each portion is shown in FIG. 16 and FIG. 17.

FIG. 18 shows a slotted trocar inserted into the lumen of a sheath with a wire depicted to illustrate the lumen of the trocar.

FIG. 19 illustrates that the lumen of a trocar may extends from a proximal end to a distal end.

FIG. 21B shows an expanded view of the tip of a tip capture trocar.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
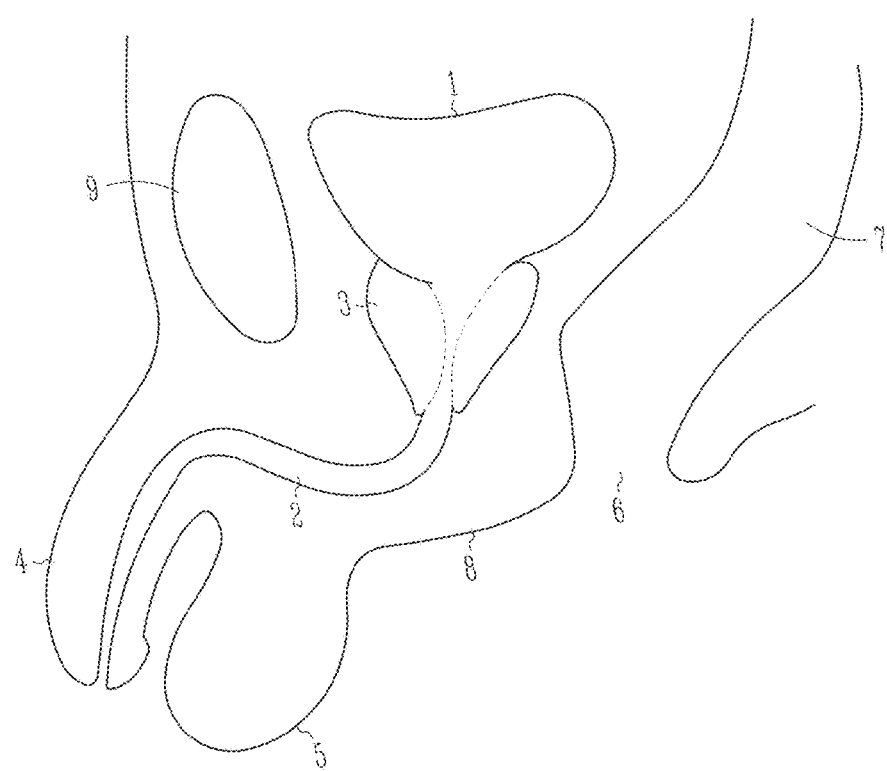
FIG. 1 is a sagittal or side view cross section showing male anatomy.

FIG. 1 is a sagittal or side view cross section showing male anatomy. The bladder 1 is connected to the urethra 2 which exits at the penis 4. A prostate gland 3 surrounds the urethra 2 near the base of the bladder 4. The urethral lumen within the prostate is shown as being constricted either by Benign Prostatic Hyperplasia (BPH) which is treated by TURP or prostate cancer which is treated by radical prostatectomy. Also shown is the scrotum 5 and perineum 8, which is the skin behind the scrotum, the anus 6 which is the opening to the rectum 7, and the pubic bone 9.

Figure 2:
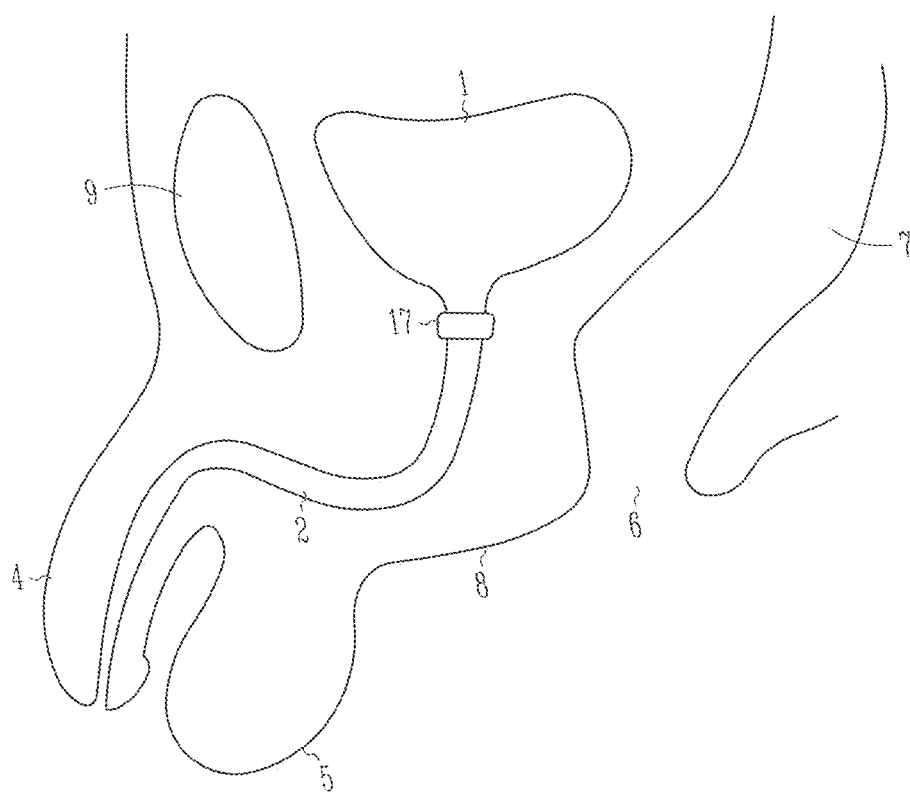
FIG. 2 is a side view cross section showing male anatomy after a radical prostatectomy.

FIG. 2 is a side view cross section showing male anatomy after a radical prostatectomy. In some embodiments, the prostate is removed during radical prostatectomy and the cut urethra is brought up and a urethral-vesical anastomosis 17 is provided to the bladder neck with sutures or staples. Removal of the prostate can damage the surrounding or adjacent tissue including the urinary sphincter and/or its enervation, resulting in incontinence due to a loss of coaptation of the urethra. One way to increase the coaptation is through the use of tissue bulking devices, such as the implantable devices described in U.S. Pat. Nos. 6,045,498, 5,964,806, 6,579,224, and 6,419,624 and their related patents and applications, the descriptions of which are hereby incorporated in their entirety.

Figure 3:
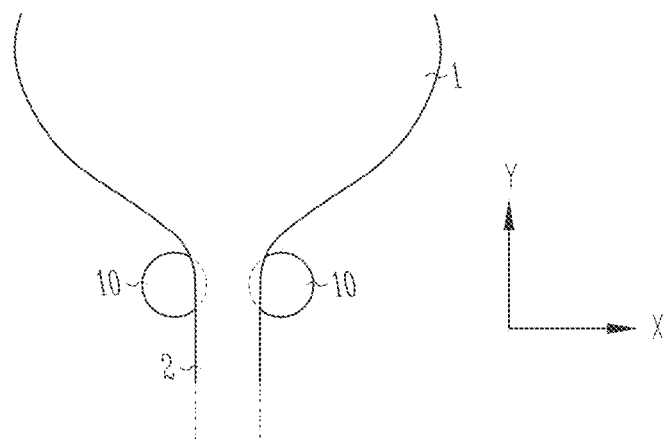
FIG. 3 is a top view showing approximate target sites of placement of implantable devices to improve coaptation of a urethra.

FIG. 3 is a top view of the bladder 1 and urethra 2 showing approximate target sites of placement of implantable devices 10 to improve coaptation of a urethra, according to one embodiment of present subject matter. The orientation of the y-axis is along the direction of the urethra 2 in the approximate location of implantation. The location is near the bladder neck and urethral vesical anastomosis in the case of radical prostatectomy or further down the urethra at the apex of the prostate after TURP.

Figure 4:
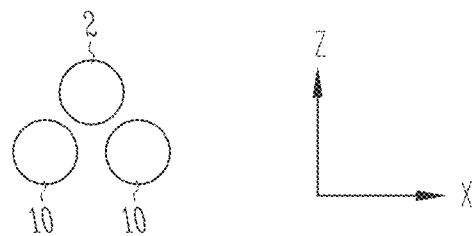
FIG. 4 is a view along the length of the urethra in the area of implantation showing approximate target sites of placement of implantable devices to improve coaptation of a urethra.

FIG. 4 is a view along the length of the urethra 2 in the area of implantation (or along the y-axis) showing approximate target sites of placement of implantable devices 10 to improve coaptation of a urethra, according to one embodiment of present subject matter. One of the difficulties addressed by the teachings provided herein is to assist in the proper location of the implantable devices 10. In particular, the accurate placement of the implantable devices 10 along the z-axis (sagittal view) is facilitated by the teachings of the present subject matter.

Figure 5:
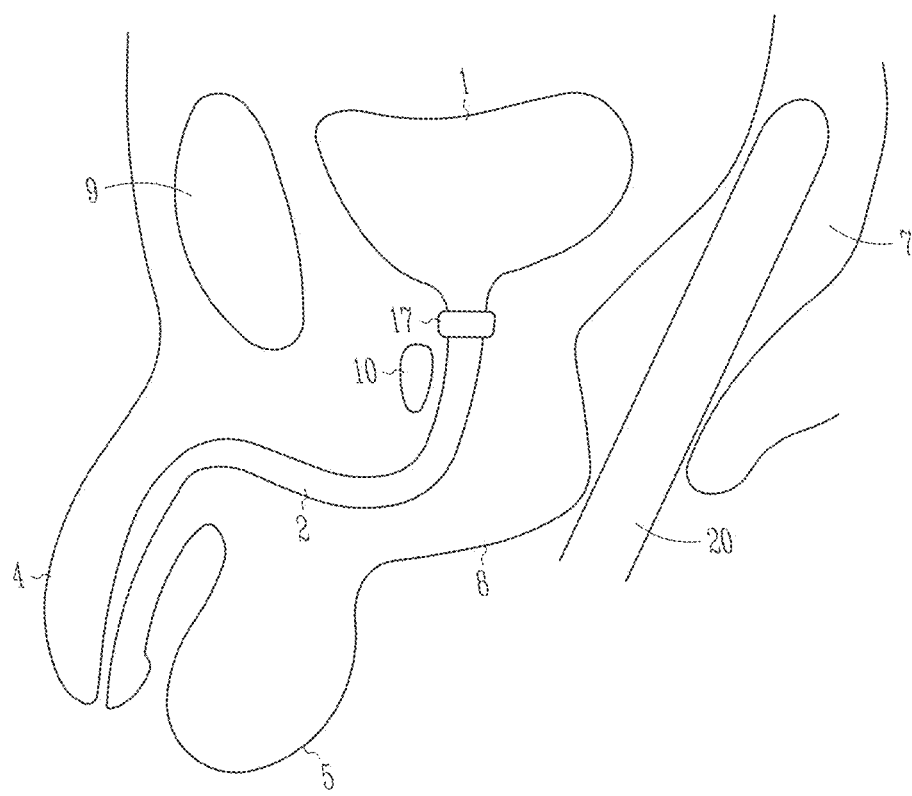
FIG. 5 is a side view cross section showing approximate placement of implantable devices in patients after radical prostatectomy.

FIG. 5 is a side view cross section showing approximate placement of implantable devices 10 in patients after radical prostatectomy, according to one embodiment of the present subject matter. It is understood that implantable devices may be placed in different positions without departing from the scope of the present subject matter. Thus, it is understood that the positions shown in the figures are intended to demonstrate the present subject matter, but are not intended in an exclusive or limited sense.

One advantage of a biplanar ultrasonic rectal probe is that it can provide planar images of tissue both longitudinally in the XY plane and radially from the rectal ultrasound probe in the rectum parallel to the urethra in the XZ plane. This facilitates placement of the devices at the target site with respect to the position of the urethra and bladder.

Figure 6:
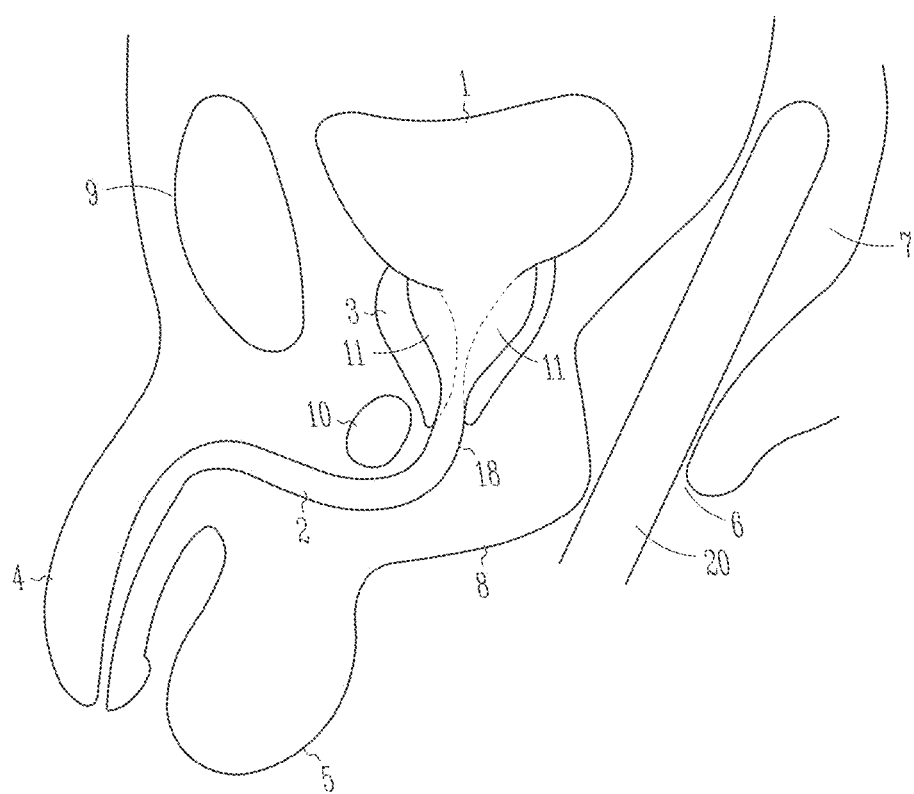
FIG. 6 is a side view cross section showing approximate placement of an implantable device after Trans-Urethral Resection of the Prostate (TURP). "11" indicates where tissue has been removed.

FIG. 6 is a side view cross section showing approximate placement of implantable devices, according to one embodiment of the present subject matter. For patients with a full or partial prostate gland 3 after TURP, the expandable portion of each implantable device 10 can be placed along the urethra near the apex of the prostate 18 to increase tissue bulking and coaptation in that area. An ultrasonic probe 20 can be inserted into the rectum 7 via the anus 6 to assist in imaging the locations of the implantable devices 10. FIG. 6 shows a prostrate gland 3 after TURP and areas 11 indicating resected portion of the prostrate.

Figure 9:
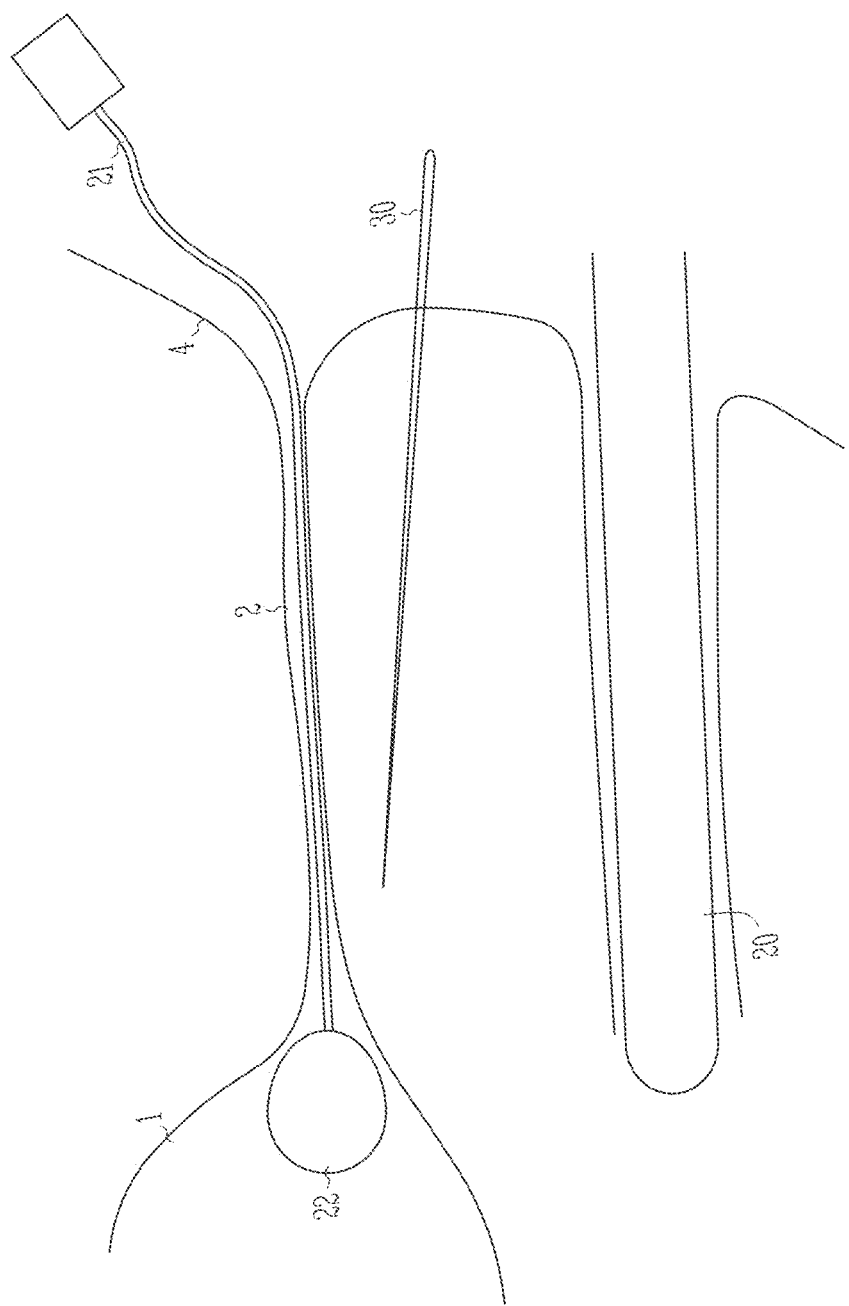
FIG. 9 shows one application of the present subject matter to a patient.

FIG. 9 shows one application of the present subject matter to a patient. An ultrasonic rectal probe 20 is used in conjunction with a Foley catheter 21 placed in the urethra with the Foley balloon 22 inflated in the bladder 1 to assist in visualizing the bladder neck and urethra 2. In such applications a doctor can rotate the rectal probe 20 to get a picture of the placement of devices with respect to the urethra in an axial segment. By rotating the probe the doctor can image the bladder neck, proximal urethra and the Foley balloon 22 sitting in the bladder neck. The doctor can also get an image of any delivery devices 30 used to deliver fluid to the target location of where the expandable portion of the implant and delivery instruments for the device itself are to be located. In various applications water can be used. Water is echogenic, so it better shows the target location of the expandable portion of the implantable device 10. In various uses the water is combined with an analgesic, such as lidocaine. In some embodiments, water with or without an analgesic can be injected at the site intended for the expandable portion of the implantable device 10 to create a pocket in the tissue so that the expandable portion will tend to stay in that position during and after inflation without migrating. This process is called "hydrodissection."

In one embodiment, the following process is employed to image the target location and accurately place the devices. It is understood that differences in method steps, order of steps, and apparatus can be made without departing from the scope of the present subject matter.

A Foley catheter is inserted into the urethra and the Foley balloon is inflated with water in the bladder neck.

An ultrasonic probe is inserted into the rectum of the patient.

The doctor uses the ultrasonic probe to image the urethra and bladder neck using the echogenetic Foley balloon as a landmark.

A small puncture in the skin in the perineum is made.

The doctor chooses a target tissue site near the bladder neck for radical prostatectomy or the apex of the prostate for TURP for placement of analgesic and fluid for hydrodissection of the targeted tissue site.

The doctor inserts a delivery device such as a needle into the small puncture of the perineum and, under ultrasonic visual guidance alternating between radial and longitudinal views as needed, tunnels through the tissue adjacent the urethra. As that delivery device is advanced the doctor may inject anesthetic or analgesic along the path, thus allowing the procedure to be done under local anesthesia.

Once at the intended delivery site more fluid can be injected to create a bolus for hydrodissection of the tissue in preparation for delivery of the expandable device.

A delivery device, e.g., a slotted trocar/sheath assembly as described herein, is inserted, and used to deliver the implantable device.

The expandable portion of the implantable device is accurately positioned at the target site.

The implantable device is then adjusted for proper coaptation.

For devices with a septum, the septum is placed under the skin. If the procedure is done under local anesthesia the site for the septum is first anesthetized with analgesic via a needle and syringe. Such devices allow for straightforward postoperative adjustment of the urethral coaptation The other side of the urethra is then treated using the same or similar procedure.

It is understood that a doctor may manipulate the delivery device with one hand and the ultrasound with the other to get continuous imaging and feedback. The doctor can also continuously switch back and forth between a radial view and a longitudinal view using, e.g., biplanar ultrasound, to ensure that the delivery device and/or implantable device is at the right distance along the urethra or from the urethra.

Various delivery devices in various embodiments can be used to introduce the echogenic fluid and place the expandable portion of the implantable devices.

It is understood that a variety of different trocar, guidewire, stylet, needle, and/or sheath combinations may be used without departing from the scope of the present subject matter. Furthermore, in various embodiments different fluid channels and Luer connections may be employed to deliver fluid to the intended target site. Additionally, delivery methods using wires placed using slotted sheaths, trocars, and/or other assemblies may be employed to deliver implantable devices to the intended target sites. It is also understood that certain embodiments of implantable devices may include openings or apertures that accommodate a pushrod or other wire to place the implantable devices in tissue at desired target sites. It is further contemplated that one or more implantable devices can be used to enhance coaptation and that the number of devices is not limited to those demonstrated herein. It is understood that delivery devices of various dimensions may be employed to achieve proper placement of the implantable device and septa of such devices.

In one embodiment, the initial approach to the delivery site for the expandable element and hydrodissection at the site is made with a spinal needle. The needle is then used to deliver echogenic fluid and/or anesthetic or analgesic (if needed). The needle is then withdrawn and replaced, again under guidance, with a device for delivering. In one embodiment, this device includes a pointed trocar within a removable sheath. In one embodiment, the trocar is hollow along its full length. In some embodiments, the sheath remains while the trocar is removed to provide a tool for delivery of the implantable device. In some embodiments a splittable sheath is used. Other embodiments are possible without departing from the scope of the present subject matter.

Figure 7:
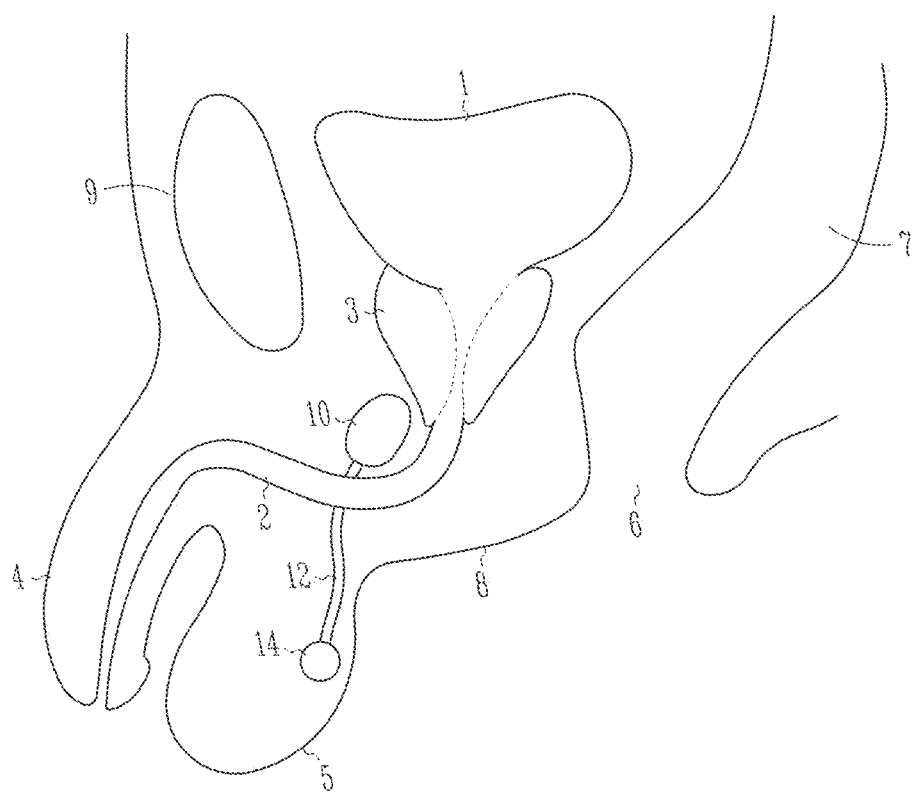
FIG. 7 is a side view cross section showing approximate placement of an implantable device including their septa after Trans-Urethral Resection of the Prostate (TURP).

FIG. 7 is a side view cross section showing approximate placement of implantable devices 10 including their septa 14 (in such embodiments), after TURP according to one embodiment of the present subject matter. It is understood that the septa 14 can be placed in various tissue locations, such as the scrotum 5 or somewhere in the perineal region 8. Subcutaneous placement of the septa provide for postoperative adjustment of the implantable devices by accessing the septum through the skin with a hypodermic needle. Coaptation can be adjusted by any of the procedures provided in the references incorporated by reference herein. For example, a cystoscope can be inserted into the urethra 2 to measure coaptation. Other devices, placements, and approaches are possible without departing from the present subject matter.

Figure 8:
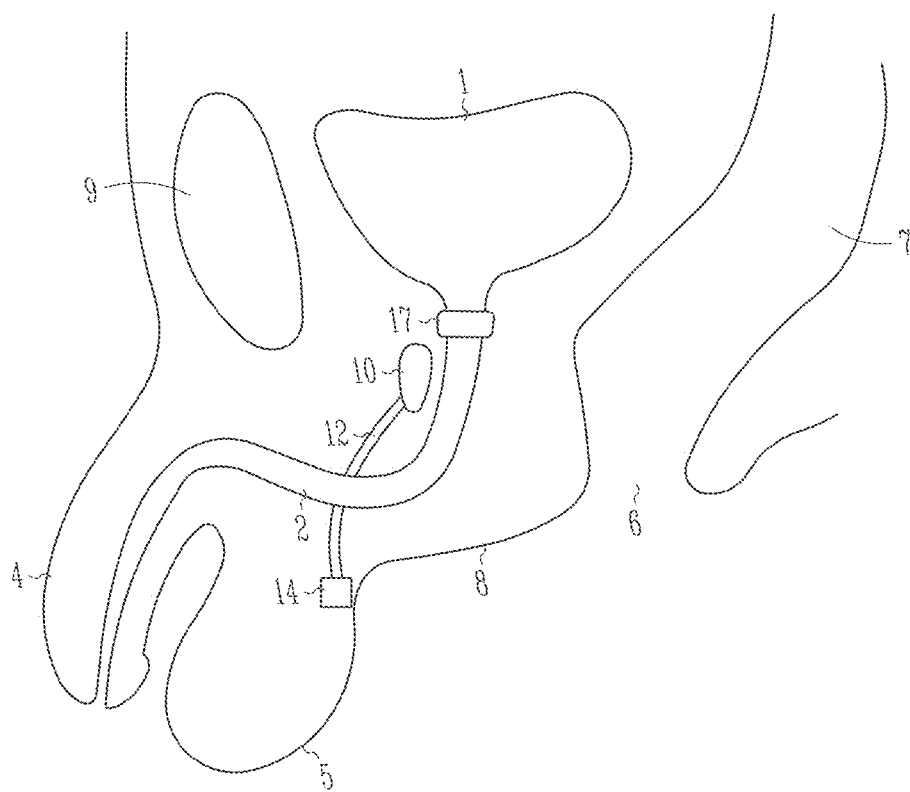
FIG. 8 is a side view cross section showing approximate placement of an implantable device including their septa after radical prostatectomy.

FIG. 8 is a side view cross section showing approximate placement of implantable devices 10 including their septa 14 (in such embodiments), after radical prostatectomy according to one embodiment of the present subject matter. It is understood that the septa 14 can be placed in various tissue locations, such as the scrotum 5 or somewhere in the perineal region 8. Subcutaneous placement of the septa provide for postoperative adjustment of the implantable devices. Coaptation can be adjusted by any of the procedures provided in the references incorporated by reference herein. For example, a cystoscope can be inserted into the urethra 2 to measure coaptation. Other devices, placements, and approaches are possible without departing from the present subject matter. Various embodiments include components that are disposable, that is that are sterilizable but not necessarily resterilizable. Such components may be made from polymers such as polyethylene, polypropylene or polytetrafluoroethylene.

A trocar includes an elongate member (shaft) and a handle portion. In various embodiments, the trocar is reusable (e.g., can be resterilized). The elongate member, in various embodiments, is sterilizable. In additional embodiments, the handle portion is also sterilizable. In another embodiment, the trocar includes steam sterilizable components. Various embodiments incorporate materials known to provide for such function, such as surgical grade stainless steel. Multiple embodiments are contemplated by the present subject matter. In each embodiment, one or more materials are used in constructing elongate member. In each embodiment, one or more materials are used in constructing handle portion.

The trocar has a proximal end and a distal end, in various embodiments. In one embodiment, a handle portion is located at a proximal end. In one embodiment, the trocar includes a sharp, e.g., beveled, tip, at a distal end. The tip is useful for penetrating tissue of a patient, according to one embodiment, such as when a doctor grasps the handle and maneuvers the trocar, distal portion first, through an incision and to an implant site located proximal a bladder neck of a patient.

A sheath includes an elongate member (shaft) and a handle portion. The elongate member is trough (U- or C-) shaped across its diameter, in one embodiment. In, various embodiments, the elongate member includes tubing which has a slot opening running at least part of the way down its length. The elongate member has a cross section which is curved in various embodiments. As such, these embodiments define an interior space of the sheath. In various embodiments, a removable trocar is sized for slidable disposition in the elongate member of the sheath, via an opening in the handle of the sheath. In various embodiments, one or more materials are used in constructing elongate member of the sheath. In each embodiment, one or more materials are used in constructing handle portion of the sheath. In various embodiments, materials include, but are not limited to, stainless steel and other materials not expressly recited herein.

Figure 16:
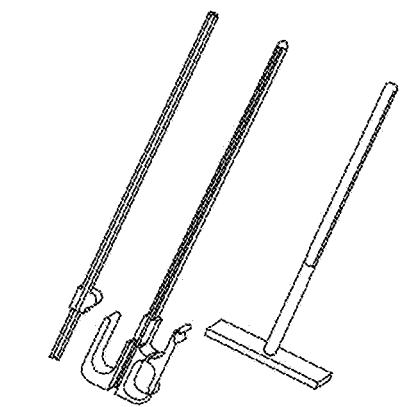
Figure 17:
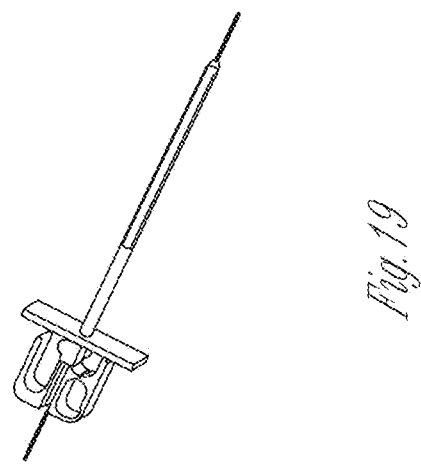
Figure 18:
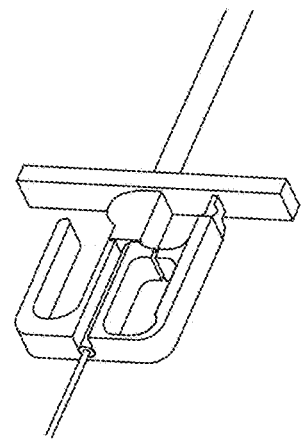

In one embodiment, the trocar shaft (housing), once assembled if it is a mated slotted trocar (FIGS. 14-19), has an elongate shape with an inner lumen suitable for passage, e.g., of a wire. In various example embodiments, the trocar is assembled from two or more longitudinally matched (mated) pieces (portions or parts). For example, one portion may have a distal receptacle (nose) (FIG. 16) for the distal end (tab) of the second portion (FIG. 17) and an optional handle. In another example, one portion may include a distal receptacle (nose) for the distal end (tab) of the second portion which second portion optionally includes a handle. However, other various example embodiments may include mating configurations of multiple sections of instruments having the same diameter. This mate or self-alignment of the first and second trocar portions may be accomplished by other means familiar to one skilled in the art such as, but not limited to, a tapered diameter trocar, a circular or rectangular funnel shaped endpoint on the receiving trocar.

Figure 19:
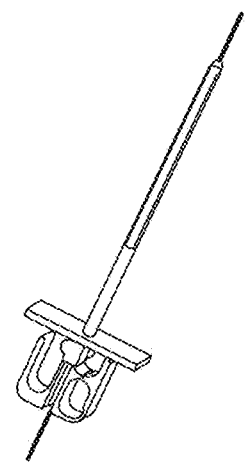

The trocar is inserted into a U-shaped sheath (FIG. 18), and a tube, wiring, and/or other device(s) may be routed through the lumen of the trocar (FIG. 19). This allows for a continuous subcutaneous path through first and second trocar portions for the placement of the aforementioned tubing, wiring, and/or any other physical connection media between the first and second incisions. After the trocar portion is removed and the sheath remains and is employed to deliver the implantable device. Other mechanical, electromechanical, or electronic guidance means can be placed on or around the trocar to aid positioning before or during blind-mating or self-alignment.

The methods of using the slotted trocar/sheath assembly include administering an anesthetic, e.g., a local anesthetic. The methods also include preparing radiopaque contrast media such that the media can be used for radiographic monitoring during surgery. In one embodiment, normal saline may be used for use. Saline, contrast, and other materials are used to expand an implantable adjustable expandable genitourinary device. One embodiment includes cleaning and sterilizing surgical tools.

Various embodiments include inserting a trocar into a sheath. In various embodiments, the doctor is to insert the trocar/sheath assembly into an incision. In various embodiments, when the tip of the implantation instrument reaches the target site below the bladder neck, the trocar is removed. In one embodiment, this is done while maintaining position of sheath tip at desired adjustable continence balloon implant location.

In one embodiment, the doctor has access to a variety of elongate implantable devices, such as those described in U.S. Pat. Nos. 6,045,498, and 5,964,806, which are incorporated herein by reference. In one embodiment, three devices of different lengths are provided, although more or less than three devices having different lengths can be provided. In various embodiments, based on the surgery and the relevant physiology, the doctor selects an adjustable continence device with the appropriate length such that a balloon of the device can be located proximal the bladder, and the adjustment chamber including a septum, such as a self sealing septum, can be located proximal the incision.

One embodiment includes inserting an implantable adjustable device through the sheath and into the patient proximal the exterior of the bladder and proximal the bladder neck of the bladder. Various embodiments advance the adjustable continence device with the balloon deflated through the sheath to the selected position using a push wire. In one embodiment, it is helpful to ensure the push wire is fully inserted in the adjustable continence device. In one embodiment, the position of the tip of the device can be confirmed by, for example, fluoroscopy, cystoscopy or palpation. The tip of the device is positioned underneath the bladder neck, in one embodiment.

Figure 20:
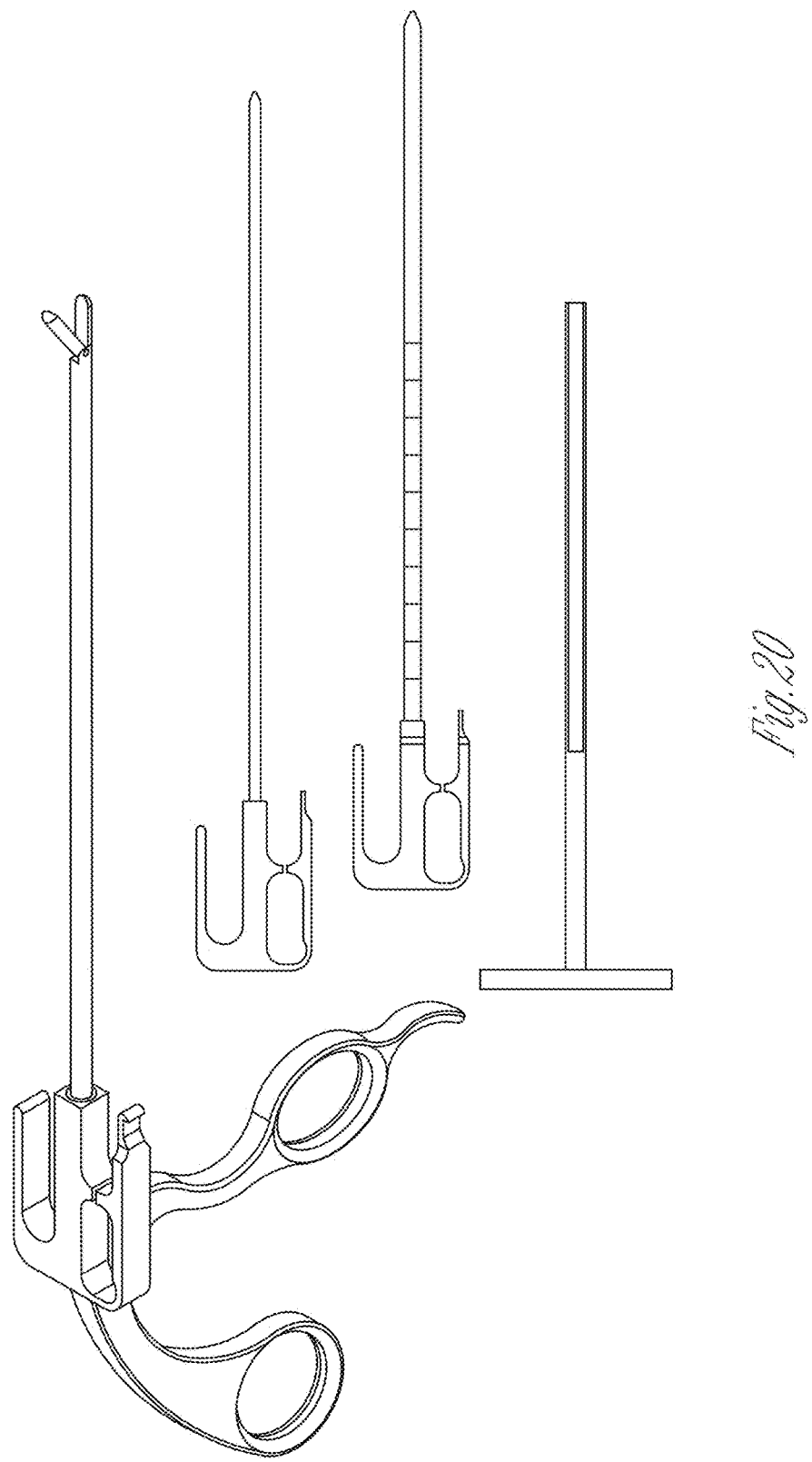
FIG. 20 shows exemplary slotted trocars and sheaths and TED.

FIG. 20 shows, among other things, a tissue expanding device for use in the methods.

Various methods include pulling the sheath back about 2 centimeters such that the balloon is clear of the sheath. This is to, in part, ensure that the balloon is not damaged during inflation. Various embodiments include, adjusting the implantable adjustable device. In various embodiments, the doctor penetrates the port septum with a needle of a syringe, such as a 23 gauge non-coring needle on the syringe, and inflates the adjustable continence balloon with fluid, such as with approximately 1 milliliter of normal saline or isotonic contrast solution. In embodiments using x-ray visualization or ultrasound, the doctor can view the balloon assuming a spherical shape. One embodiment includes removing the sheath completely from the patient before inflation.

In one embodiment using two or more implantable adjustable devices, the doctor is to leave the push wire in place and to perform a similar procedure for other devices. In embodiments using two devices contralateral to another with respect to the patient, the doctor is to proceed in the same way with the contralateral side.

In examples where it is possible, the doctor is to confirm symmetrical positioning of the adjustable continence balloons with respect to the urethra such as by radiology or by ultrasound. When a doctor determines that the location of implantable devices is acceptable, they can remove the push wires from both adjustable continence devices after balloon inflation.

When both adjustable continence devices are in position and have been inflated, the doctor can remove the Foley catheter, if one was used. In one embodiment, the doctor can check for continence with a stress test. If the patient remains incontinent after the stress test, one embodiment allows for an increase in the volume of one or both balloons in increments, such as by 0.5 milliliter increments using the saline or isotonic contrast solution until continence is confirmed. Some devices provide for up to 2.0 milliliter per balloon, but the present subject matter is not so limited. For example, the balloon may initially have about 1.5 milliliters per balloon and then increments of, for example 2 milliliters, are added up to about 8 to 12 milliliters per balloon. In some optional examples, the doctor confirms the absence of urethral or bladder injury by cystoscopic examination.

Various embodiments provide for the doctor to create a pocket in the contralateral side in the same manner. For a male patient, a pocket is created in the scrotum to receive the port and a pocket is created in the contralateral side to receive the other port. In some of these embodiments, the doctor places the remaining adjustable continence device port in this pocket. In one embodiment, the doctor checks to verify that the tubing of the adjustable continence devices is not kinked unacceptably.

Exemplary Transrectal Ultrasound (TRUS) Assisted Over the Wire (OTW) Implantation Procedure.

Figure 10:
FIG. 10 shows a patient in the lithotomy position. A Foley catheter is inserted and the bladder is filled with 40-50 mL of saline solution. Two horizontal 0.5- to 1-cm skin incisions are made in the perineum about 1 cm lateral to the median line and about 1.5 cm above the rectum.
Figure 11:
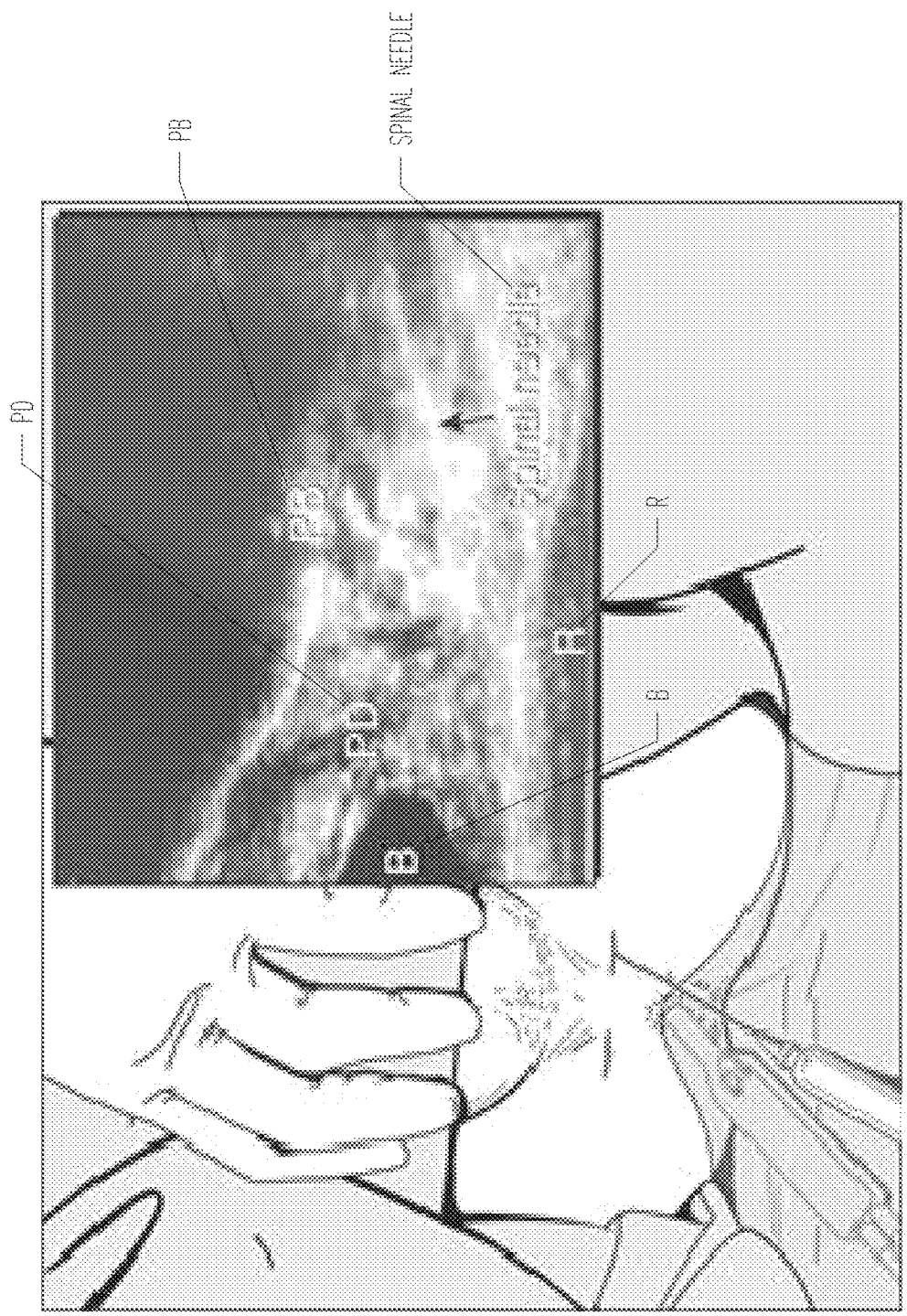
FIG. 11 shows insertion of a needle proximal to a target site. Deep local anesthesia is administered with the needle, e.g., a 20-gauge spinal needle, which is inserted through skin incisions and then directed bilaterally to the vesicourethral anastomosis under biplanar transrectal ultrasound guidance (as shown in the box). A linear probe monitors advancement of the 20-gauge spinal needle towards the bladder neck, while the convex probe monitors the distance from the urethra. The anaesthetic is released along the needle path in the subcutaneous tissue in the pelvic diaphragm and laterally to the anastomosis, creating the space for an implanted device by a mechanism of hydrodissection. A guidewire, e.g., with a J-tip, is placed through the needle. The tip, e.g., a J-tip, extends beyond the tip of the needle. B=bladder; PB=pubic bone; PD=pelvic diaphragm; R=rectum.

The patient is placed in the lithotomy position and the lower abdomen, genitalia, perineum, and the perianal area are disinfected. A 14- or 16-Ch Foley catheter is inserted in the bladder, which is filled with 40-50 mL of saline solution to clearly visualize the urethra and the bladder neck with TRUS. The scrotum is held above the perineum with tape. The anal ring is isolated from the perineum with a drape and TRUS is performed using a 7.5-MHz linear probe and a small convex probe. When local anesthesia only is used, 10 mL of ropivacaine 7.5 mg/mL may be administered with a regular 20-gauge needle in skin and subcutaneous tissue at 1-2-cm intervals bilaterally around the intended perineal incisions. Two horizontal 0.5-1-cm skin incisions may be made in the perineum about 1 cm lateral to the median line and about 1.5 cm above the rectum (FIG. 10). Deep local anesthesia is then to be administered with 20 mL of ropivacaine 7.5 mg/mL. For example, a 20-gauge spinal needle is inserted through the skin incisions and directed bilaterally to the vesicourethral anastomosis under biplanar (e.g., longitudinal to coronal) TRUS guidance (FIG. 11). The linear probe monitors advancement of the 20-gauge spinal needle towards the bladder neck, while the convex probe is used to monitor the distance from the urethra. The anesthetic is released along the needle path in the subcutaneous tissue, in the pelvic diaphragm, and laterally to the anastomosis, creating the space for implantable device by hydrodissection. A guidewire or stylet is placed next to or through the needle, and the needle is removed.

Figure 12:
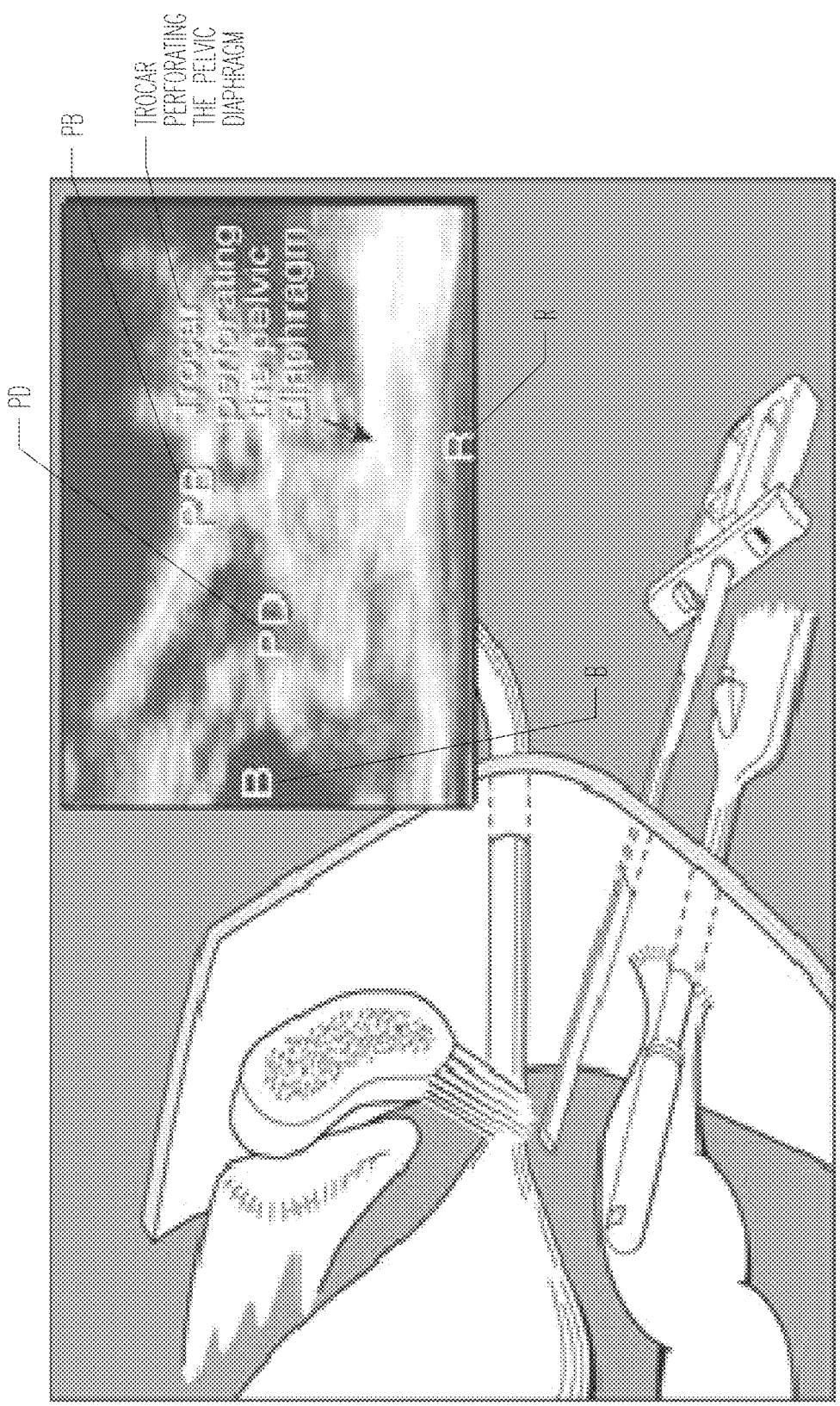
FIG. 12 illustrates introduction of a trocar/sheath assembly under transrectal ultrasound (TRUS) guidance (as shown in the box). The sharp-tipped, removable trocar contained within a U-shaped sheath is inserted over the guidewire. A rotating action (twisting motion) may be employed to perforate the pelvic diaphragm and advance the trocar over the wire towards the hydrodissected tissue, e.g., scar tissue, at the level of anastomosis on one side of the bladder neck.
Figure 21A:
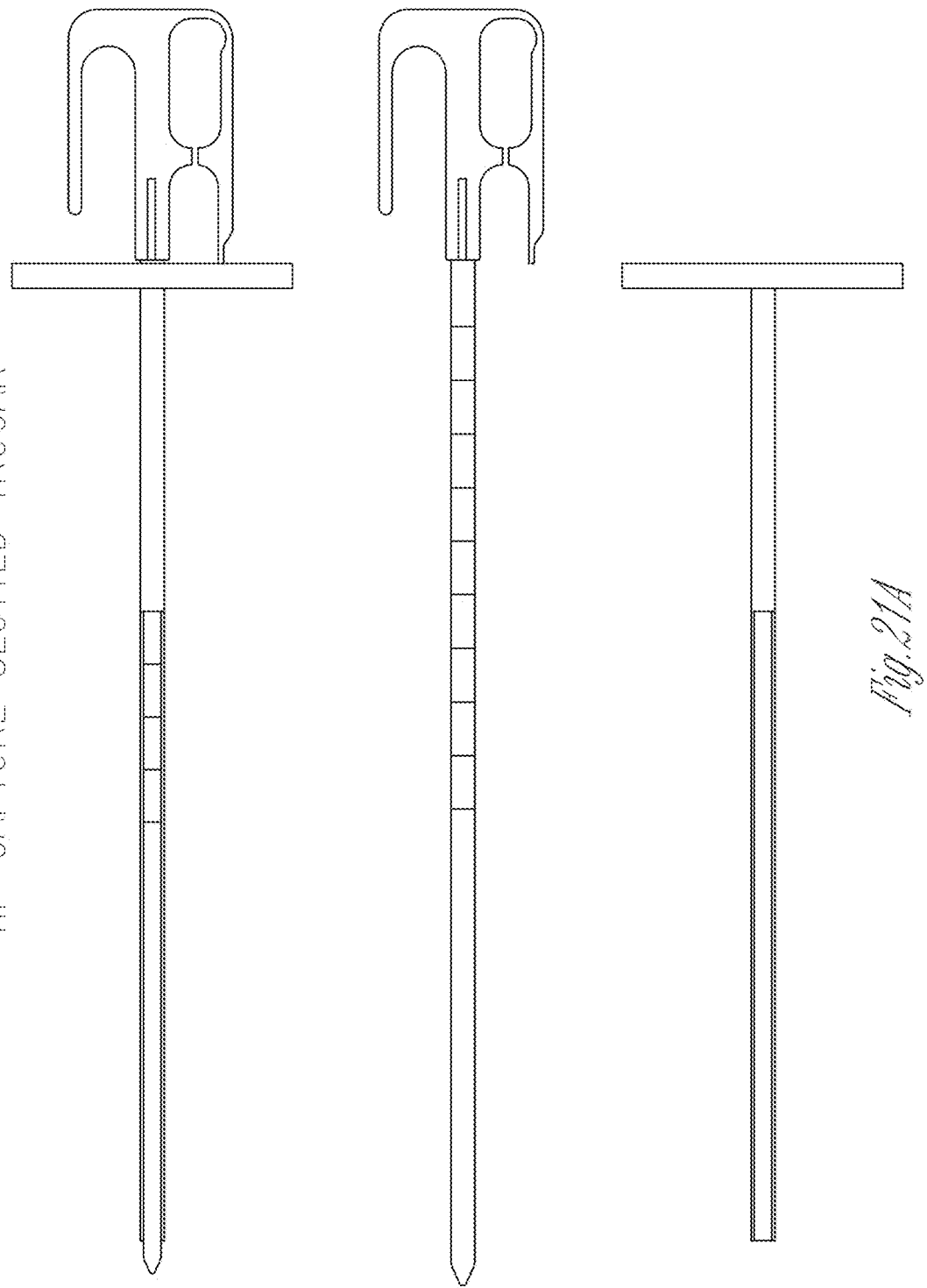
FIG. 21A illustrates one example of a tip capture slotted trocar and sheath, and the assembly thereof.
Figure 21B:
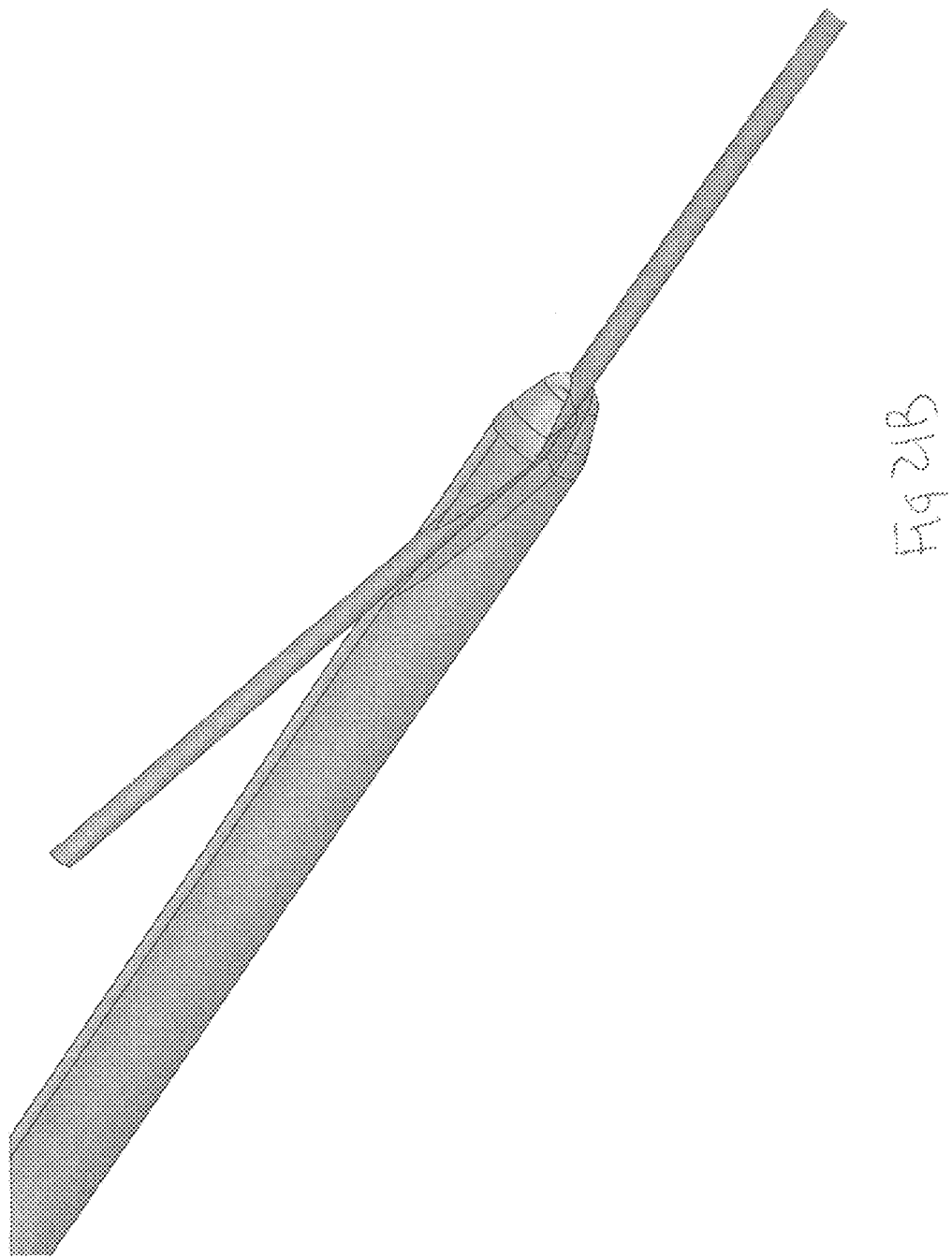
FIG. 21B is a close up view of a tip capture slotted trocar.

Under TRUS guidance, a trocar and sheath assembly, e.g., a sharp or blunt tipped, removable trocar, e.g., a mated trocar or a tip capture trocar (FIGS. 21A and 21B), contained within a U-shaped sheath, is inserted over the wire through the skin incision. A twisting motion is employed to perforate the pelvic diaphragm and advance the trocar towards the hydrodissected scar tissue at the level of anastomosis on one side of the bladder neck. The position of the trocar and sheath may be confirmed by TRUS (FIG. 12). The trocar and wire are removed, leaving the U-shaped sheath in place. During this maneuver the sheath may be gently advanced about 0.5 cm to occupy the space created by the trocar tip.

Figure 13:
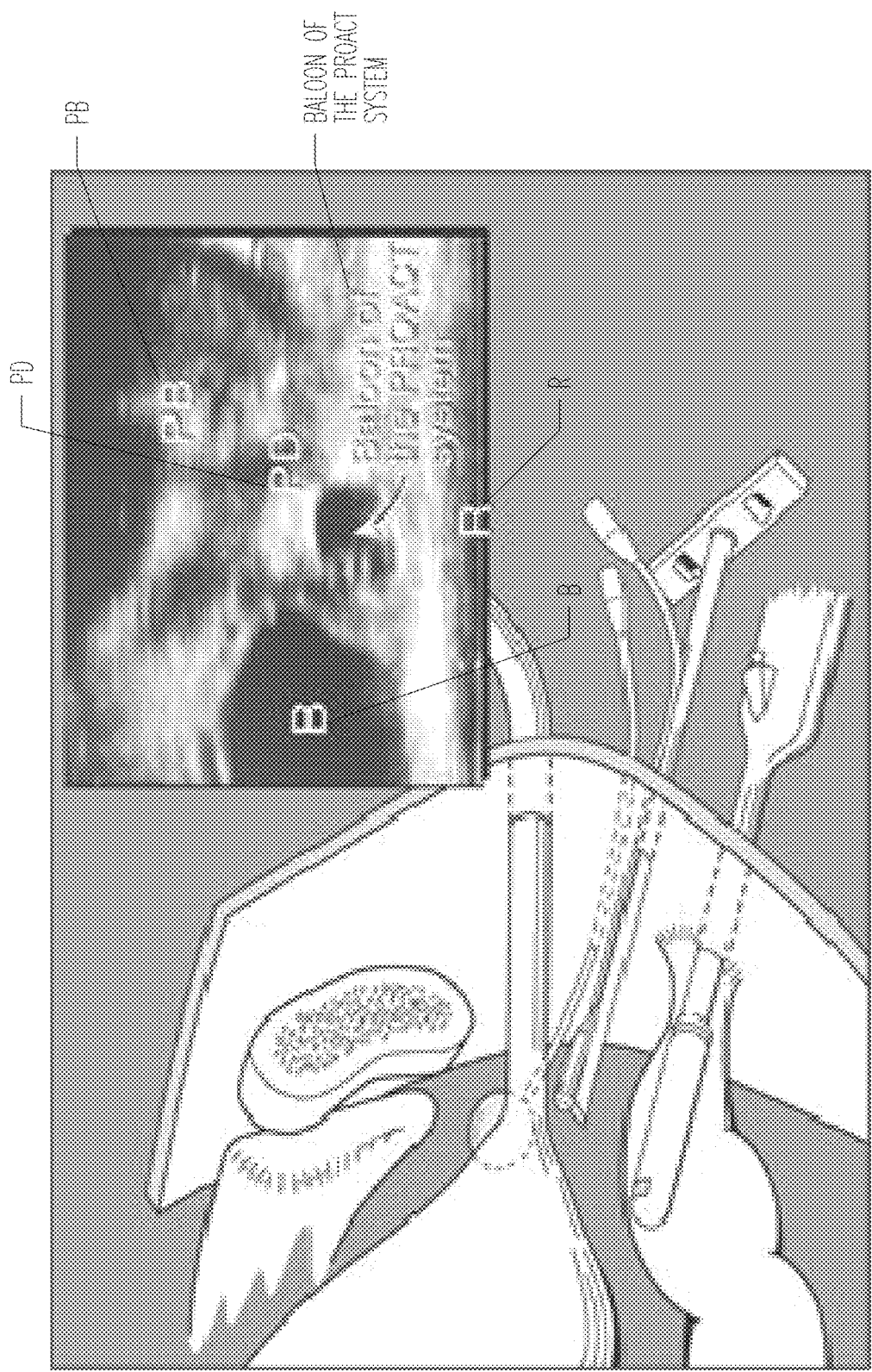
FIG. 13 illustrates trocar removal, leaving the U-shaped sheath in place. The internal channel of the sheath is lubricated using sterile gel and with the help of a push wire, the implantable device is passed along the sheath into position at the bladder neck. The balloon is inflated with 1 mL normal saline, e.g., 0.9% saline, solution via the titanium port. Transrectal ultrasound is used to confirm correct balloon placement, as shown in the box. B=bladder; PB=pubic bone; PD=pelvic diaphragm; R=rectum.
Figure 14:
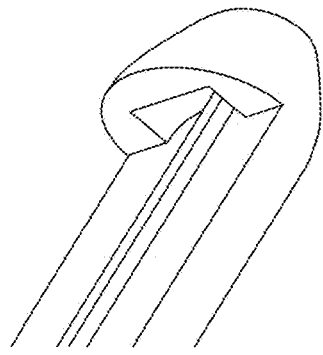
FIGS. 14-19 show exemplary slotted trocars and sheaths, and assembly thereof.
Figure 15:
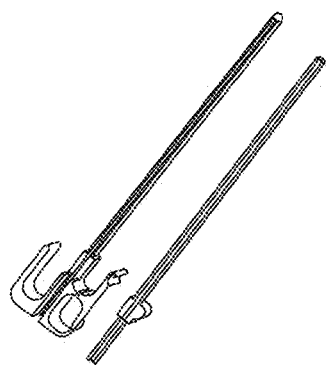

The internal channel of the sheath is then lubricated using a sterile gel. With the help of a push wire, an implantable device is passed along the sheath into position at the bladder neck. The sheath is withdrawn approximately 2 cm to permit balloon expansion as it is inflated with, for instance, 1 mL normal saline solution via the titanium port (FIG. 13). TRUS may be used to confirm correct balloon placement in all planes (linear probe to establish proximity to the bladder neck and convex probe to assess balloon position laterally in relation to the urethra). Exemplary balloon placement is considered as being 5-10 mm proximal to the bladder neck and 2-5 mm lateral from the urethra. In one embodiment, the balloons are placed at 9 o'clock and 3 o'clock in relation to the urethra to create a triangular coaptation of the urethra between the two balloons and the symphysis pubis. The push wire is then removed. Using scissors or a Kelly clamp, a subcutaneous parascrotal tunnel is fashioned to allow placement of the conduit tube and titanium port. The tunnel should be sufficiently sized to ensure that the balloon tubing is not looped or kinked and the port can lie in a supine position. The procedure may be repeated on the contralateral side. The incisions are closed in two layers with 4-0 resorbable sutures.

The trocar and/or sheath may be reusable (resterilizable). The trocar, e.g., mated, bore hole or tip capture trocar, or the portions of a mated trocar, or sheath are cleaned and sterilized before and after each use. For example, the trocar and sheath components are immersed and soaked in warm tap water (20-40° C.) and pH neutralized enzymatic detergent for 10 minutes. For 5 minutes, all individual components are scrubbed with a soft bristle brush to visually remove soil. For 30 seconds, the components are thoroughly rinsed with warm water (20-40° C.). For 10 minutes, the components are ultrasonically cleaned in room temperature purified water and pH neutral enzymatic detergent. For 1 minute, the components are thoroughly rinsed with room temperature purified water. The components are dried using low linting, non-abrasive soft cloth. For sterilization, the components are steam sterilized using a prevacuum cycle at 132°-135° C. (275° F.) for a minimum of three (3) minutes. Prior to use, the instrument is reassembled by placing the "tab" of one portion of the trocar into the nose of the other portion of the trocar, and the tabbed portion is lowered into the handle, after which the assembled slotted trocar is inserted in the U-channel sheath.

In one embodiment, the invention thus provides a slotted trocar for "over the wire" use with a sheath and a needle, for assisting in the placement of an implantable device adjacent a body lumen. In one embodiment, a needle, e.g., a spinal needle, e.g., a 20 gauge needle, is inserted into an incision adjacent a body lumen and the needle is advanced using TRUS that includes a linear probe and a convex probe. Anesthetic is delivered through the needle along the path of advancement and once the needle is placed at target site for an implantable device placement using TRUS, hydrodissection is employed to create space for the implantable device. The needle is used to place a guidewire or stylet, and then the needle is withdrawn leaving the guidewire or stylet which is used to guide the assembled trocar and a channeled sheath ("over the wire") into the space previously occupied by the needle. The trocar may have a sharp distal end and force is employed to advance the assembled trocar/sheath combination. In one embodiment, the trocar may have a blunt distal end and force is employed to advance the assembled trocar/sheath combination. TRUS is employed to verify position of the trocar/sheath device. The trocar is withdrawn and the sheath is slightly advanced to occupy the space created. The inner channel of the sheath is lubricated prior to advancing the implantable device in the channel, e.g., using a push wire. The sheath is retracted slightly about 1-2 cm, to allow for balloon expansion.

In one embodiment, a slotted trocar is formed by assembly of at least two trocar parts. Each part has a convex outer surface and a concave inner surface which inner surface once assembled, forms a channel (lumen) of less than about 1 mm (e.g., 0.04 inches or less) in diameter for a guidewire, e.g., one which may be about 0.035 to 0.038 inches in diameter. In one embodiment, the trocar is formed of a material that can be sterilized and reused, e.g., stainless steel. After assembly of the trocar, it is inserted into a sheath with a U-shaped channel. The sheath may formed of a material that can be sterilized and reused, e.g., stainless steel.

Exemplary Transrectal Ultrasound (TRUS) Assisted Over the Needle (OTN) Implantation Procedure.

The patient is placed in the lithotomy position and the lower abdomen, genitalia, perineum, and the perianal area are disinfected. A 14- or 16-Ch Foley catheter is inserted in the bladder, which is filled with 40-50 mL of saline solution to clearly visualize the urethra and the bladder neck with TRUS. The scrotum is held above the perineum with tape. The anal ring is isolated from the perineum with a drape and TRUS is performed using a biplanar probe having a 7.5-MHz linear probe and a small convex probe. When local anesthesia only is used, 10 mL of ropivacaine 7.5 mg/mL may be administered with a regular 20-gauge needle in skin and subcutaneous tissue at 1-2-cm intervals bilaterally around the intended perineal incisions. Two horizontal 0.5-1-cm skin incisions may be made in the perineum about 1 cm lateral to the median line and about 1.5 cm above the rectum. Deep local anesthesia is then to be administered with 20 mL of ropivacaine 7.5 mg/mL. For example, a 20-gauge needle, e.g., one having a hub adapted for a syringe, a removable hub or a hubless needle, is inserted through the skin incisions and directed bilaterally to the vesicourethral anastomosis under multiplanar TRUS guidance. The linear probe monitors advancement of the 20-gauge spinal needle towards the bladder neck, while the convex probe is used to monitor the distance from the urethra. The anesthetic is released along the needle path in the subcutaneous tissue, in the pelvic diaphragm, and laterally to the anastomosis, creating the space for implantable device by hydrodissection.

Under TRUS guidance, a trocar and sheath assembly, e.g., bore hole, slotted or tip capture trocar, contained within a U-shaped sheath, is inserted over or adjacent to the needle through the skin incision. In one embodiment, an assembly having a bore hole trocar or slotted trocar is inserted over or adjacent to a hubless needle or a needle with a removable hub (so that the internal lumen can pass over the needle). In one embodiment, an assembly having a tip capture trocar is inserted over or adjacent to a hubbed needle. A twisting motion is employed to perforate the pelvic diaphragm and advance the trocar towards the hydrodissected scar tissue at the level of anastomosis on one side of the bladder neck. The position of the trocar and sheath may be confirmed by TRUS. The trocar and the needle are removed, leaving the U-shaped sheath in place. During this maneuver the sheath may be gently advanced about 0.5 cm to occupy the space created by the trocar tip.

The internal channel of the sheath is then lubricated using a sterile gel. With the help of a push wire, an implantable device is passed along the sheath into position at the bladder neck. The sheath is withdrawn approximately 2 cm to permit balloon expansion as it is inflated with, for instance, 1 mL 0.9% saline solution via the titanium port. TRUS may be used to confirm correct balloon placement in all planes (linear probe to establish proximity to the bladder neck and convex probe to assess balloon position laterally in relation to the urethra). Exemplary balloon placement is considered as being 5-10 mm proximal to the bladder neck and 2-5 mm lateral from the urethra. In one embodiment, the balloons are placed at 9 o'clock and 3 o'clock in relation to the urethra to create a triangular coaptation of the urethra between the two balloons and the symphysis pubis. The push wire is then removed. Using scissors or a Kelly clamp, a subcutaneous parascrotal tunnel is fashioned to allow placement of the conduit tube and titanium port. The tunnel should be sufficiently sized to ensure that the balloon tubing is not looped or kinked and the port can lie in a supine position. The procedure may be repeated on the contralateral side. The incisions are closed in two layers with 4-0 resorbable sutures.

The trocar and/or sheath may be reusable (resterilizable). The trocar or the portions of the mated slotted trocar or sheath are cleaned and sterilized before and after each use. For example, the trocar and sheath components are immersed and soaked in warm tap water (20-40° C.) and pH neutralized enzymatic detergent for 10 minutes. For 5 minutes, all individual components are scrubbed with a soft bristle brush to visually remove soil. For 30 seconds, the components are thoroughly rinsed with warm water (20-40° C.). For 10 minutes, the components are ultrasonically cleaned in room temperature purified water and pH neutral enzymatic detergent. For 1 minute, the components are thoroughly rinsed with room temperature purified water. The components are dried using low linting, non-abrasive soft cloth. For sterilization, the components are steam sterilized using a prevacuum cycle at 132°-135° C. (275° F.) for a minimum of three (3) minutes. Prior to use, the instrument is reassembled by placing the "tab" of one portion of the trocar into the nose of the other portion of the trocar, and the shaft is lowered into the handle, after which the assembled slotted trocar is inserted in the U-channel sheath.

In one embodiment, the invention thus provides a slotted trocar for "over the needle" use with a sheath, for assisting in the placement of an implantable device adjacent a body lumen. In one embodiment, a needle, e.g., a spinal needle, e.g., a 20 gauge needle, is inserted into an incision adjacent a body lumen and the needle is advanced using TRUS that includes a linear probe and a convex probe. Anesthetic is delivered through the needle along the path of advancement and once the needle is placed at target site for an implantable device placement using TRUS, hydrodissection is employed to create space for the implantable device. The needle is used to guide the trocar and a channeled sheath into the space previously occupied by the needle. The trocar may have a sharp distal end and force is employed to advance the assembled trocar/sheath combination. In one embodiment, the trocar may have a blunt distal end and force is employed to advance the assembled trocar/sheath combination. TRUS is employed to verify position of the trocar/sheath device. The trocar and needle are withdrawn and the sheath is slightly advanced to occupy the space created. The inner channel of the sheath is lubricated prior to advancing the implantable device in the channel, e.g., using a push wire. The sheath is retracted slightly about 1-2 cm, e.g., using TRUS, to allow for balloon expansion.

In one embodiment, the slotted trocar is formed by assembly of at least two trocar parts. Each part has a convex outer surface and a concave inner surface which inner surface once assembled, forms a channel (lumen) of less than about 1 mm (about 0.05 inches or less, e.g., 0.04 inches or less) in diameter for a guidewire, e.g., one which may be about 0.035 to 0.038 inches in diameter. In one embodiment, the trocar is formed of a material that can be sterilized and reused, e.g., stainless steel. After assembly of the trocar, it is inserted into a sheath with a U-shaped channel. The sheath may formed of a material that can be sterilized and reused, e.g., stainless steel.

While the method and apparatus provided herein are demonstrated for application to the male, it is understood that they are applicable to female applications as well. Likewise they are applicable in general to provide coaptation to other lumens within the body such as the anal canal and rectum or the esophagus.

It is understood that various implantable devices may be employed. The imaging of such devices may be enhanced by adding echogenic coating or elements within the expandable portion. Various imaging methods may include temporarily filling the expandable portion with air to provide enhanced visibility via ultrasound. Other approaches are possible without departing from the scope of the present subject matter.

This application is intended to cover adaptations and variations of the present subject matter. It is to be understood that the above description is intended to be illustrative, and not restrictive. The scope of the present subject matter should be determined with reference to the appended claim, along with the full scope of legal equivalents to which the claims are entitled.

What is claimed is:

1. A method for implanting an implantable adjustable device to improve coaptation of the urethra at a target site for controllable coaptation of a patient's urethra, comprising:
    placing a small puncture in the perineum of the patient;
    passing a needle through the puncture, while optionally delivering anesthetic or analgesic during passage, to the target site under ultrasonic guidance;
    placing at a position a guidewire or stylet through or adjacent to the needle while the needle is at the target site, withdrawing the needle while leaving the guidewire or stylet at the position, delivering a mated trocar or a tip capture trocar and a U-shaped sheath assembly over the guidewire or stylet to the target site after the needle is withdrawn, and removing the mated trocar or the tip capture trocar while leaving the sheath at the target site, wherein the U-shaped sheath has an interior space and is configured to fit over the outer circumference of the mated or the tip capture trocar, and wherein the mated trocar is formed of at least two longitudinally mated portions that, once assembled, form an inner lumen; and
    delivering the implantable adjustable device via the interior space of the U-shaped sheath.

2. The method of claim 1, further comprising injecting echogenic fluid at the target site adjacent the urethra, wherein the echogenic fluid comprises an anesthetic or analgesic fluid.

3. The method of claim 1, further comprising injecting a fluid at the target site including hydrodissecting the target site with the fluid to create a pocket for the implantable device.

4. The method of claim 1, wherein the U-shaped sheath assembly is delivered to the target site under ultrasonic guidance.

5. The method of claim 1, wherein the guidewire or stylet is placed through the needle.

6. The method of claim 1, wherein the inner lumen of the mated trocar has a diameter of less than about 1.0 mm.

7. The method of claim 1, wherein the mated trocar or the tip capture trocar and the U-shaped sheath assembly are placed proximal to an exterior of a bladder of the patient and proximal to a bladder neck of the bladder.

8. The method of claim 1, wherein the implantable device comprises an adjustable device comprising an adjustable balloon connected to a self sealing port via a conduit.

9. The method of claim 1, wherein a first portion of the mated trocar has a recess at a distal end and a second portion has a tab that is configured to fit into the recess, wherein the U-shaped sheath is sized to removably and slidably receive the mated trocar, the sheath including a slot running at least partially along a first portion and defining the interior space, and a second portion defining a lumen, wherein the interior space and the lumen are sized to slidably receive the mated trocar and the implantable adjustable device.

10. A system configured for implanting an adjustable continence device into a patient having a bladder with a bladder neck, the adjustable continence device comprising an adjustable balloon and a self sealing port, the system comprising:
- a mated trocar including a length and a width, the trocar coupled to a handle and configured and sized to extend at least from an incision in the patient to the bladder neck of the patient, wherein the mated trocar is formed of at least two mated portions that once assembled form an inner lumen, wherein a first portion of the mated trocar has a recess at a distal end and a second portion of the mated trocar has a tab extending at the distal end that is configured to fit into the recess; and
- a U-shaped sheath defining an interior space sized to removably and slidably receive the mated trocar, the sheath including a slot running at least partially along a first portion and defining the interior space, and a second tube shaped portion defining a second lumen.

11. The system of claim 10, wherein the interior space is sized to slidably receive the mated trocar and the adjustable continence device has a lumen comprising a pushwire.

12. The system of claim 10, wherein the mated trocar once assembled includes a sharp tip, with the handle being at a proximal end of the mated trocar.

13. The system of claim 10, wherein the handle is on one of the two mated portions.

14. A method for implanting an implantable adjustable device to improve coaptation of the urethra at a target site for controllable coaptation of a patient's urethra, comprising:
- placing a small puncture in the perineum of the patient;
- passing a needle through the puncture, while optionally delivering anesthetic or analgesic during passage, to the target site under ultrasonic guidance;
- delivering a mated trocar and a U-shaped sheath assembly over or adjacent to the needle to the target site while the needle is at the target site, and removing the trocar and the needle while leaving the sheath at the target site, wherein the U-shaped sheath has an interior space and is configured to fit over the outer circumference of the mated trocar and wherein the mated trocar is formed of at least two longitudinally mated portions that, once assembled, form an inner lumen, wherein a first portion of the mated trocar has a recess at a distal end and a second portion of the mated trocar has a tab extending at the distal end that is configured to fit into the recess; and
- delivering the implantable adjustable device via the interior space of the U-shaped sheath.

15. The method of claim 14, wherein the needle that is employed with the mated trocar is a hubless needle or a needle with a removable hub.

16. The method of claim 14, wherein the needle is a hubbed needle.

17. The method of claim 14, further comprising injecting echogenic fluid at the target site adjacent the urethra, wherein the echogenic fluid comprises an anesthetic or analgesic fluid.

18. The method of claim 14, further comprising injecting a fluid at the target site including hydrodissecting the target site with the fluid to create a pocket for the implantable device.

19. The method of claim 14, wherein the U-shaped sheath assembly is delivered to the target site under ultrasonic guidance.

20. The method of claim 14, wherein the mated trocar and the U-shaped sheath assembly are placed proximal to an exterior of a bladder of the patient and proximal to a bladder neck of the bladder.

21. The method of claim 14, wherein the implantable device comprises an adjustable device comprising an adjustable balloon connected to a self sealing port via a conduit.

\* \* \* \* \*